United States Patent [19]

Ger

[11] Patent Number: 4,919,152
[45] Date of Patent: Apr. 24, 1990

[54] METHOD OF CLOSING THE OPENING OF A HERNIAL SAC

[76] Inventor: Ralph Ger, 16 Oaks Hunt Rd., Lake Success, N.Y.

[21] Appl. No.: 195,586

[22] Filed: May 18, 1988

Related U.S. Application Data

[63] Continuation of Ser. No. 20,555, Mar. 2, 1987, abandoned, which is a continuation of Ser. No. 815,659, Dec. 30, 1985, abandoned, which is a continuation of Ser. No. 525,125, Aug. 22, 1983, abandoned.

[51] Int. Cl.⁵ .............................................. A61B 17/10
[52] U.S. Cl. ...................................... 128/898; 606/142
[58] Field of Search ............... 128/337, 334 R, 334 C, 128/335, 898

[56] References Cited

U.S. PATENT DOCUMENTS

| | | |
|---|---|---|
| 641,036 | 1/1900 | Pilling . |
| 2,011,169 | 8/1935 | Wappler . |
| 2,034,785 | 3/1936 | Wappler . |
| 2,384,697 | 9/1945 | Riccardi . |
| 3,585,985 | 6/1971 | Gould . |
| 3,882,854 | 5/1975 | Hulka et al. . |
| 4,038,987 | 8/1977 | Komiya ................................ 128/321 |
| 4,049,002 | 9/1977 | Kletschka et al. . |
| 4,122,856 | 10/1978 | Mosior et al. . |
| 4,235,238 | 11/1980 | Ogiu et al. ........................ 128/335 X |
| 4,257,419 | 3/1981 | Goltner et al. . |
| 4,273,129 | 6/1981 | Boebel . |
| 4,424,810 | 1/1984 | Jewusiak . |
| 4,485,953 | 12/1984 | Rothfuss ...................... 128/334 R X |
| 4,595,007 | 6/1986 | Mericle ............................ 128/334 R |

FOREIGN PATENT DOCUMENTS

| | | |
|---|---|---|
| 293929 | 9/1916 | Fed. Rep. of Germany . |
| 2330182 | 1/1975 | Fed. Rep. of Germany . |
| 2553540 | 6/1977 | Fed. Rep. of Germany . |

OTHER PUBLICATIONS

Ger, Ralph, "The Management of Certain Abdominal Herniae by Intra-Abdominal Closure of the Neck of the Sac", Annals of the Royal College of Surgeons of England, pp. 342-344, Sep. 1982.

*Primary Examiner*—Michael H. Thaler
*Attorney, Agent, or Firm*—Rosen, Dainow & Jacobs

[57] ABSTRACT

Disclosed is an improved surgical instrument useful in indirect hernia for closing sacs having narrow neck openings. The instrument is formed of a tubular body and has manual drive extending therethrough to actuate a pair of jaws at an end of the tubular body between open and closed positions. The instrument is formed with a conduit and valve which provide suction at the remote end of the instrument in the immediate vicinity of the jaws.

14 Claims, 4 Drawing Sheets

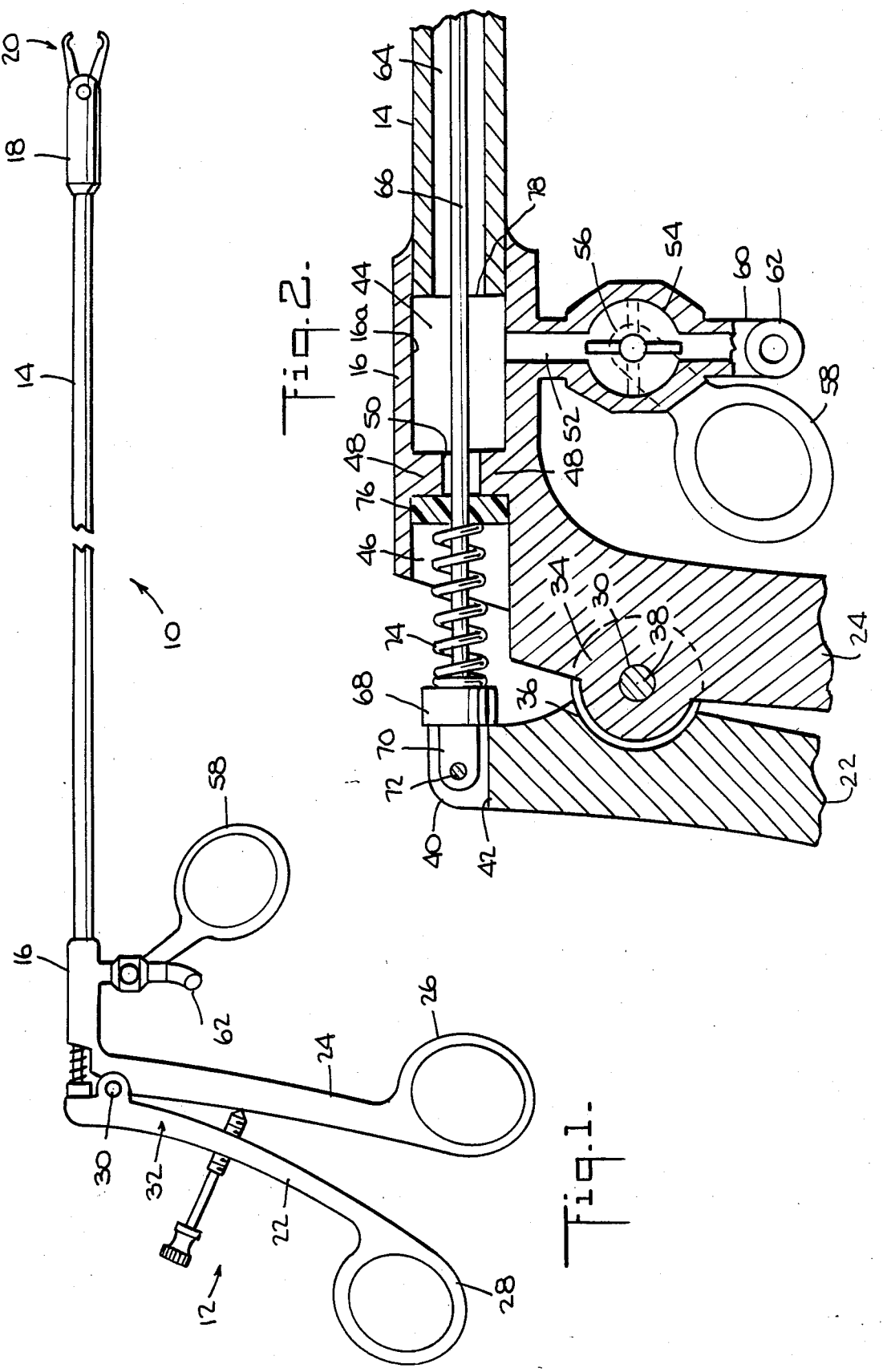

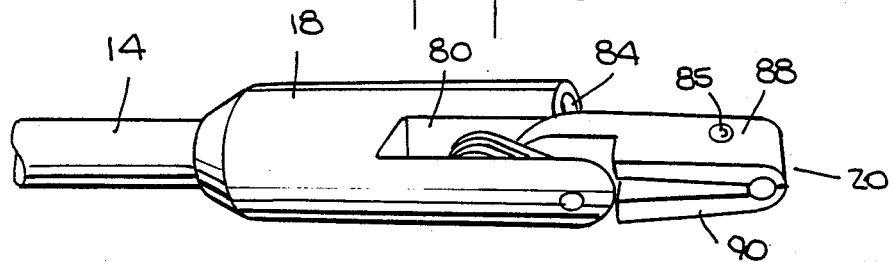
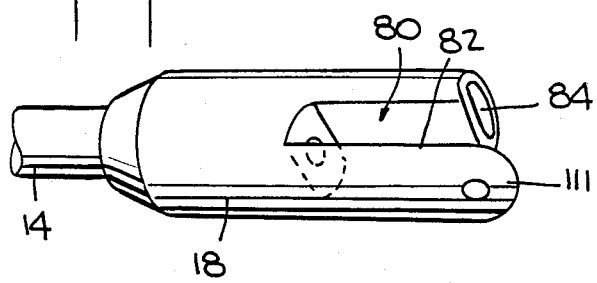
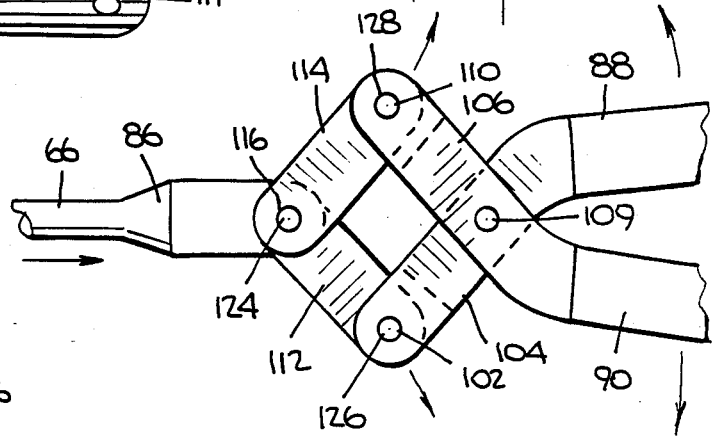
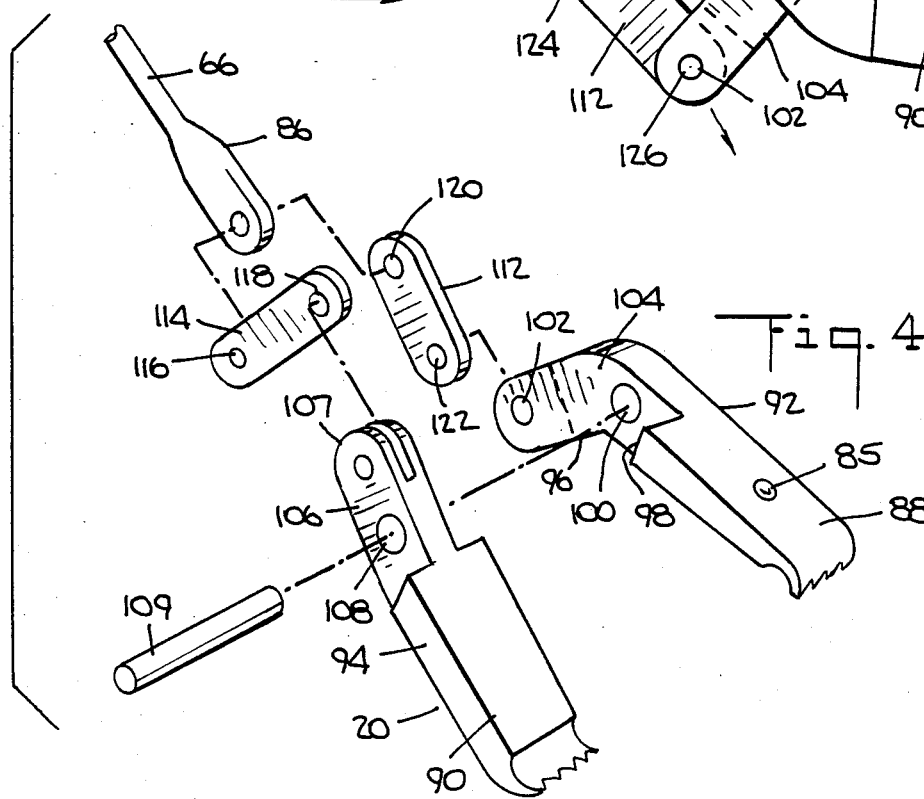

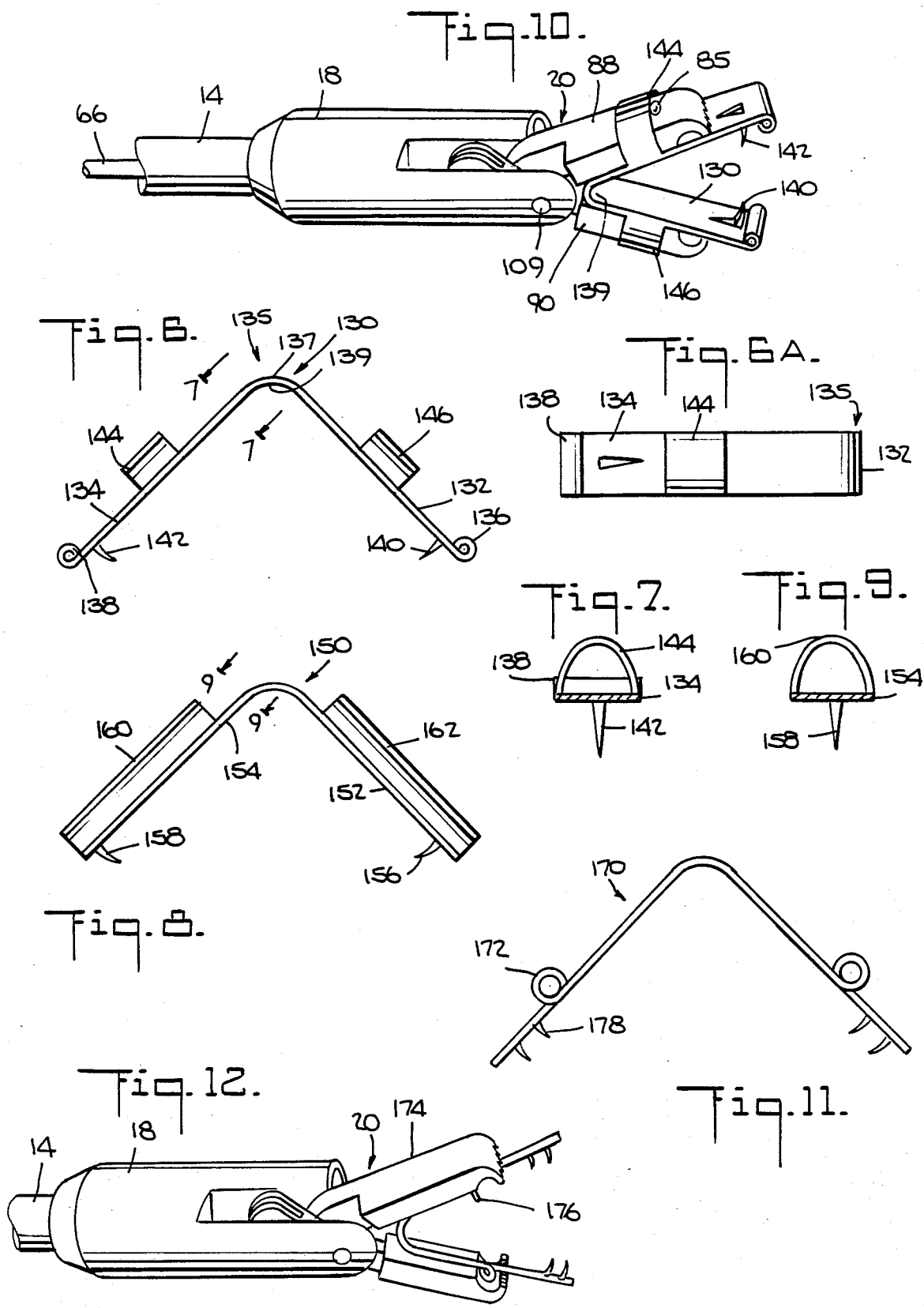

METHOD OF CLOSING THE OPENING OF A HERNIAL SAC

This is a continuation, of application Ser. No. 020,555, filed March 2, 1987, now abandoned, which is a continuation of Ser. No. 815,659, filed December 30, 1985 now abandoned which is continuation of Ser. No. 525,125, filed August 22, 1983, now abandoned.

BACKGROUND OF THE INVENTION

The present invention concerns a system and apparatus for closing the abdominal opening of the sac of an indirect hernia, and more generally for closing sacs having narrow neck openings.

The problem of herniation is one that may be experienced by men, women and children of either sex and generally relates to the abnormal protrusion of an organ or part of an organ or a portion of tissue through an aperture in its containing cavity. The usual hernia treated by this system is congenital in origin, although it tends to manifest throughout life from infancy to old age. Increased intra-abdominal tension may or may not play a part in the development of the herniation.

The treatment of a hernia inevitably involves surgery wherein the area of the hernia is opened, the contents of the hernia are replaced, and the opening closed by suture material. Obviously such a procedure leaves a rather large and sometimes unattractive scar at the incision site which is generally in the groin area. More importantly the surgery carries a long list of both general and local complications, both immediate and delayed, including a small number of fatalities.

SUMMARY OF THE INVENTION

The present invention is a system and apparatus for closing the narrow neck of the sac responsible for the clinical syndrome of indirect herniae. A salient aspect of the present invention is that it obviates a major operation with all the major and minor complications accompanying such a procedure, including mortality, and replaces it with a minor operation whose incisions are limited to puncture wounds.

The new surgical instrument has an elongated tubular section which encloses and houses a pushrod which engages a pair of jaws at the end of the instrument. When activated the push rod opens and closes these jaws. The elongated tubular section is supported by an enlarged chamber of the housing through which the pushrod extends. At a lower section of the chamber is a port accessing a two-position valve which is in communication with a suction source. The valve has a local actuator. A conduit extends from the valve to the forwardmost or instrument end of the apparatus.

When the pushrod is actuated the clamping jaws are driven to an opened position where they are retained by a screw. The jaws will close when pressure is released from the rod-actuating mechanism and the screw is released. Further pressure is applied by manually closing the handles. Surgical clips are positioned between the jaws when in the opened condition, and then the instrument is inserted through a canula and positioned appropriately. When the clip is opposite the sac opening, the jaws are closed by the above mechanisms and the surgical clips are applied to close the opening of the sac at its neck.

To avoid the loss of the clip from the forceps the clip may have loops on each of its legs into which the jaws of the instrument fit. In this instance, a bead on the outer surface of each jaw aids in maintaining the clip in position on the jaws. In an alternative embodiment, the clip legs are hollow and provide a sleeve into which each of the jaws is inserted. A further alternative is to hold the clip by a pin which protrudes from the upper jaw and engages a hole in the upper leg of the clip. Finally the clips extend beyond the edge of the jaws facilitating the grasping of the tissues.

The conduit, and two-position valve are useful for sucking the tissue of the sac opening into the jaws. The channel in the instrument may run adjacent to the extending tubular section which houses the pushrod, or alternatively may be coaxial with the extending tubular section as well as coextensive therewith.

The various features of novelty which characterize the invention are pointed out with particularity in the claims annexed to and forming a part of this specification. For a better understanding of the invention, its operating advantages and specific objects obtained by its use, reference should be had to the accompanying drawings and descriptive matter in which there is illustrated and described a preferred embodiment of the invention.

BRIEF DESCRIPTION OF THE DRAWINGS

FIG. 1 is a front elevation view of the new apparatus of the invention;

FIG. 2 is a fragmentary and enlarged view of the apparatus of FIG. 1;

FIG. 3 is a perspective view of the forwardmost section of the apparatus of FIG. 1;

FIG. 3A is similar to FIG. 3 with the jaw assembly removed;

FIG. 4 is a perspective view of the jaw assembly disassembled;

FIG. 5 is a side view of the assembled jaw assembly wherein the jaws are in a partially opened condition;

FIGS. 6 and 6a show front and top views of a clip of the present invention;

FIG. 7 shows a sectional view taken along line 7—7 of FIG. 6;

FIG. 8 shows a front view of an alternate clip of the present invention;

FIG. 9 shows a sectional view taken along line 9—9 of FIG. 8;

FIG. 10 shows a perspective view of the clip of FIG. 6 engaged by the jaws of FIGS. 4 and 5;

FIG. 11 shows another embodiment of the clip; and

FIG. 12 shows a pair of jaws engaging the clip of FIG. 11.

DESCRIPTION OF PREFERRED EMBODIMENT

Referring to the drawings and specifically FIG. 1, the new instrument 10 has a handle section 12 at one end, an elongated tubular section or body 14, and a tubular section 18 at the opposite end to which is attached a pair of jaws 20. The handle section 12 is formed with a pair of arms 22 and 24 connected by pivot 30 and which terminate in finger grips 26 and 28 respectively. A spring 32 biases the arms to spaced or open condition. A screw 25 is threaded through the arm 24 and a protruding pointed end of the screw 25 abuts the facing surface of the arm 22, as explained more fully hereinafter.

Referring to FIG. 2, the pivot connection 30 comprises an extending apertured circular section 34 of arm 24 which fits within a complementary area 36 of arm 22.

A similar circular section (not shown) on arm 22 is joined with section 34 by a pin 38.

Still referring to FIG. 2, the upper end of arm 22 terminates in a set-back extending wall 40 forming a ledge 42. Arm 24 terminates in the expanded part 16 defining a chamber 16a in which tubular body 14 is supported at a forward end of the chamber. As shown in FIG. 2, chamber 16a is comprised of a forward part 44 and a rear part 46 which are separated by inwardly extending walls 48 with an aperture 50 connecting the forward and rear chamber parts 44 and 46 respectively.

Extending from the underside of chamber part 46 is a port 52 which leads to a valve housing 54 wherein a petcock valve 56 is located. The petcock valve is operated by a finger grip 58 for allowing or inhibiting fluid communication with port 60 which extends from the opposite side of the valve housing and is adapted for connection to an exhaust tube 62 connected to an evacuation source (not shown).

Tubular body 14 defines an internal annular chamber 64 extending along its length. A pushrod 66 extends from the upper end 40 of arm 22 through rear and forward chamber parts 46 and 44, and through tubular section 14 into the enlarged tubular section 18 at the forward end. The rear end of pushrod 66 terminates in a flange section 68 from which extends an apertured tongue 70 fastened to the arm 22 by a pin 72 within the aperture. A return spring 74 engages the flange 68 at that face opposite the extending tongue 70 and extends to bushing 76. The return spring surrounds pushrod 66 which extends through the bushing 76 and the aperture 50 into the forward chamber 44.

FIG. 3 shows a perspective view of the front end of tubular section 14 with the enlarged portion 18. FIG. 3A shows the same perspective view of the enlarged portion with jaws 20 removed. A generally rectangular cavity 80 is formed in portion 18 from which jaws 20 extend. Cavity 80 is bounded by inward wall 82, which along with a protion of the outer wall of chamber 18 forms a conduit 84 in fluid communication with internal chamber 64. It will be appreciated that as configured conduit 84 is adaptable for fluid communication with a chamber 64 whether the latter was parallel, adjacent, coextensive or coaxial with the channel through which pushrod 66 extends.

FIG. 4 shows an exploded view of the jaws removed from the cavity 80. Pushrod 66 terminates in an extending apertured tongue 86. The jaws assembly 20 includes an upper and a lower jaw 88 and 90 respectively, which are the forwardmost sections of elements 92 and 94 respectively. The rearmost section 96 of element 92 forms a ledge 98. Section 96 has a large hole 100 and a smaller hole 102. The section 96 is formed with a slot 104 through which smaller hole 102 passes transversely. Likewise, element 94 is formed with a rear section 106 with a large hole 108 and a small hole 110. The small hole passes transversely through a slot 107 formed in section 106. A pair of links 112 and 114, each having openings 116, 118 and 120, 122 at their respective opposite ends are included in the jaw assembly as subsequently described. A pin 109 extends through opening 100 and 108 of elements 92 and 94 to rotatably connect the same within cavity 80 via opening 111 in inner wall 82.

FIG. 5 shows a front view of the assembled jaws 88 and 90 partially opened. As shown, links 112 and 114 are pivotly connected to tongue 86 by a pin 124 which extends through opening 116 of link 114, the aperture of tongue 86 and finally opening 120 of link 112. The opposite end of link 112 is rotatably connected to element 88 at opening 102 by a pin 126, while the opposite end of link 114 is rotatably connected to element 90 at opening 110 by a pin 128. As shown elements 88 and 90 are pivotably connected by pin 109. Pin 109 is opening 111 of inner wall 82 is a fixed pivot point for links 112 and 114 as will be subsequently described in regard to this toggle linkage.

FIGS. 6 to 9 show alternate forms of clips which may be used in connection with the new apparatus 10. The clip 130 of FIGS. 6 and 7 is formed of a thin section of stainless steel defining two legs 132 and 134 joined in a curved arch 135 and which may terminate in inverted ends 136 and 138 respectively. The strip is generally in the form of a V-shape having a convex outer surface 137 and concave inner surface 139. Teeth 140 and 142 extend inwardly from the inner sides of legs 132 and 134 respectively. Each leg has extending therefrom a loop 144 and 146 respectively, fashioned so that jaws 88 and 90 may individually fit within the loops as further illustrated in FIG. 10 where the jaws are in open position. FIGS. 8 and 9 show an alternate clip 150 of stainless steel formed with legs 152 and 154 having respective teeth 156 and 158 inwardly extending from the legs. Sleeves 160 and 162 extend along a portion of the length of the respective legs, and like loop 144, are fashioned to accommodate jaws 88 and 90. A pair of beads, one of which is shown by reference number 85 in FIGS. 3 and 4 may be employed to aid in maintaining the positioning of the clips on the jaws.

The present invention is used in the manner as generally illustrated in FIG. 10. A relatively small incision of approximately ½ inch is made in the abdominal wall. The clip 130 or 150 is positioned on the open jaws 88 and 90 of the instrument 10. These jaws are actuated or opened in the following manner. Finger grips 26, 28, are spread open by manually exerting outwardly directed forces on the grips 26, 28 or by turning the screw 25 to separate the arms 22, 24. Spreading the arms 22, 24 apart causes the push rod 26 to move linearly toward the jaw assembly 20 from a retracted or first position to an extended or second position. When the arms 22, 24 are manually spread apart, the screw 25 is then manually turned until the pointed end thereof is set against the arm 24 as illustrated in FIG. 1. Thus, the spread-apart position of the arms 22, 24 is maintained by the screw 25 until the screw 25 is released. The linear movement of the pushrod 66 results because tongue 70 is pinned to wall 40 of arm 22. The forward movement of pushrod 66 pushes tongue 86 into the jaw assembly causing links 112 and 114 to pivot. Since pin 109 is fixed, pins 126 and 128 move in opposite directions causing jaws 88 and 90 to open. Movement of the arm 22 to the spread apart position causes compression of the spring 74 between the flange section 68 and the bushing 76. Thus, the spring 74 exerts a force which would reverse the spread apart condition of the arms 22, 24 if the screw 25 were not set against the arm 24, or a manual force were not continuously exerted to keep the arms 22, 24 apart. The clip 130 or 150 is placed on the jaws 88 and 90 by engagement of the jaws with loops 144 and 146 or loops 160 and 162.

An alternate version of the clip is shown in FIGS. 11 and 12, wherein a wire is formed into a generally V-shape 170 with a small loop 172 on each leg to be engaged and releasably secured in the jaws 174 by pin 176 extending from one jaw. This will prevent accidental dislodgement of the clip during emplacement. The clip extends beyond the ends of the jaws of the forceps and beyond the end 184 of the suction tube opening so that application of the clip is not impeded. To enable efficient grasping of tissue this clip has dual hooklets 178 extending generally inward from each leg.

In practice, the instrument is slim and elongated so that the body part 14 has a length dimension of no less than twelve inches to 300 mm. and an outside diameter no greater than 6.5 mm. so that it can readily pass through a typical endoscope. In the closed position, the maximum dimension across the jaws is also no greater than 6.5 mm; the opened jaws have a diameter of ½" (1.25 cm).

The loaded instrument is then inserted within a canula and maneuvered to the site of the herniation. The location of the instrument vis a vis the open sac may be monitored by conventional equipment such as a laparoscope inserted through a puncture wound in the abdomen. A slow release of finger grips 26 and 28 toward the closed position causes jaws 88 and 90 to close so that the teeth 140 and 142 or 156 and 158 of the corresponding clip may pierce the adjacent tissue of the sac opening to close the same. This slow release is effected by turning the screw 25 in a direction opposite to that used previously to set the point of the screw 25 against the arm 24. As the screw 25 is turned the compressed spring 74 acts as a linear actuator to drive the push rod 66 in the direction away from the jaw assembly 20 causing the jaws to close at a rate determined by the rate of turning the screw 25. Then the instrument is removed, reloaded and the procedure is repeated until a sufficient number of clips are in place. At appropriate times the finger grip 58 of petcock valve 56 is opened providing suction via conduit 84 from annular chamber 64, exhaust tube 62 from a suction source not shown. Such suction will suck opening tissue of the sac into the jaws for clipping. The instrument is finally withdrawn and the puncture wound sealed. It will be appreciated that the incision need only be large enough to accommodate the loaded instrument and is substantially smaller than incisions and the resulting scar in traditional herniae procedures; the incision measures 1.25 cm. maximally.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

I claim:

1. A method for closing the opening of a hernial sac having separated tissue portions in the groin area of a patient by inserting an instrument through an incision in the patient's abdominal wall, comprising the steps:
    (a) making an incision in the abdominal wall of said patient at a site in the abdomen which site is remote from said opening in said hernial sac in said groin area;
    (b) providing an instrument loaded with at least one surgical clip releasable from the instrument, said instrument being slim for entry into said abdominal incision and elongated to reach said opening of said hernial sac from said abdominal incision, said instrument having jaw elements at one end thereof, the other end of said instrument including drive means to operate the jaws reversibly from opened and closed positions;
    (c) inserting said instrument, jaw elements first, through said abdominal incision;
    (d) maneuvering said one end of the instrument to the site of the opening of said hernial sac;
    (e) grasping and approximating the edges of the separated tissue portions of said hernial sac opening; and
    (f) joining permanently said approximated edges of the tissue portions by closing said surgical clip carried by said instrument about said approximated edges.

2. A method as claimed in claim 1, comprising the further steps of separating said instrument from said closed surgical clip, and then withdrawing said instrument via said abdominal incision to be outside said abdomen.

3. A method as claimed in claim 1, comprising a further step before step (c) of inserting a cannula through said abdominal incision, step (c) being performed by passing said instrument through said cannula.

4. A method as claimed in claim 1, wherein said instrument has a length not less than 300 millimeters and an outside diameter of about 6.5 millimeters.

5. A method for closing the opening of a hernial sac having separated tissue portions in the groin area of a patient by inserting an instrument through an incision in the patient's abdominal wall comprising the steps:
    (a) making a small incision in the abdominal wall at a site in the abdomen which site is remote from the opening in said hernial sac in said groin are and through which an instrument is insertable to reach and close the opening of said hernial sac;
    (b) providing an instrument loaded with at least one surgical clip releasable from the instrument, said instrument being slim for entry into said small abdominal incision and elongated to reach said opening of said hernial sac from said small abdominal incision, said instrument having jaw elements at one end thereof, the other end of said instrument including drive means to operate the jaws reversibly from opened and closed positions;
    (c) inserting said instrument, jaw elements first, through said small abdominal incision;
    (d) maneuvering said one end of the instrument to the site of the opening of said hernial sac while said drive means remains at least partially outside of said abdominal incision;
    (e) grasping and approximating the edges of the separated tissue portions of said hernial sac opening; and
    (f) joining permanently said edges of the tissue portions by closing said surgical clip carried by said instrument about said approximated edges.

6. A method as claimed in claim 5, whereby the said other end of said instrument and said drive means remain outside said abdominal wall when the jaw elements thereof are within the abdomen at the site of the opening of said hernial sac.

7. A method according to claim 5 wherein said small incision in said abdominal wall is maximally 1.25 centimeters in length.

8. A method for closing the opening of a hernial sac having separated tissue portions in the groin area of a patient by inserting an instrument through an incision in the abdominal wall comprising the steps of:
    making a small incision through the abdominal wall of the patient at a site in the abdomen which site is remote from the opening in said hernial sac in said groin area of the patient;

inserting an elongate instrument through said abdominal incision;

moving said instrument through said abdominal incision and through the internal body cavity of the patient so that the distal end of said instrument is close to the opening in said hernial sac in said groin area of the patient while remaining on an internal side of said abdominal opening;

gripping, approximating and holding together two pieces of body tissue on opposite sides of said opening in the hernial sac from said internal side of said abdominal opening, the composite step of gripping, approximating and holding being performed remotely from tissue edges with said instrument by manual manipulation at a proximal end thereof; and joining together said two pieces of body tissue from said internal side of said abdominal opening, said step of joining being performed with said instrument by manual manipulation at a proximal end thereof.

9. A method for closing the opening of a hernial sac having separated tissue portions in the groin area of a patient by inserting an instrument through an incision in the abdominal wall, comprising the steps:
  (a) making a small incision of approximately one half inch breadth in the abdominal wall of said patient at a site in the abdomen which site is remote from said opening in said hernial sac in said groin area;
  (b) providing an instrument loaded with at least one surgical clip releasable from the instrument, said instrument being slim for entry into said abdominal incision and elongated to reach said opening of said hernial sac from said abdominal incision, said instrument having jaw elements at one end thereof, the other end of said instrument including drive means to operate the jaws reversibly between opened and closed positions;
  (c) inserting said instrument, jaw elements first, through said abdominal incision;
  (d) maneuvering said one end of the instrument from inside the abdomen to the site of the opening of said hernial sac;
  (e) grasping and approximating the edges of the separated tissue portions of said hernial sac opening by partially closing said surgical clip; and
  (f) joining permanently said approximated edges of the tissue portions by fully closing said surgical clip carried by said instrument about said approximated edges.

10. A method for closing the opening of a hernial sac having separated tissue portions in the groin area of a patient by inserting an instrument through an incision in the abdominal wall, comprising the steps;
  (a) making a small incision of approximately on half inch in the abdominal wall of said patient at a site in said abdomen which site is remote from said opening in said hernial sac in said groin;
  (b) providing an instrument loaded with at least one surgical clip releasable from the instrument, said instrument being slim for entry into said abdominal incision and elongated to reach said opening of said hernial sac from said abdominal incision, said instrument having jaw elements at one end thereof, the other end of said instrument including drive means to operate the jaws reversibly between opened and closed positions;
  (c) inserting said instrument, jaw elements first, through said abdominal incision;
  (d) maneuvering said one end of the instrument to the site of the opening of said hernial sac;
  (e) grasping and approximating the edges of the separated tissue portions of said hernial sac opening; and
  (f) joining permanently said approximated edges of the tissue portions by closing said surgical clip carried by said instrument about said approximated edges.

11. A method for a hernial repair operation for closing the neck opening of a hernial sac having separated tissue portions in the groin area of a patient, said neck opening defined by spaced apart tissue portions thereof, said method including use of an endoscope, comprising the steps:
  (a) creating a puncture wound of approximately one half inch breadth in the abdomen at a site remote from said hernial sac in the groin area,
  (b) inserting a canula through said puncture wound,
  (c) providing an instrument loaded with at least one surgical clip releasable from the instrument, said instrument being slim with a maximum outside diameter of 6.5 mm and being elongated with length of approximately twelve inches to reach said hernial sac neck opening from said puncture wound, said instrument having a pair of jaws at the end inserted through said canula into said abdomen and drive means at said opposite end for operating said jaws reversibly between open and closed positions,
  (d) inserting said instrument with the jaws end first through said canula,
  (e) maneuvering said jaws end of the instrument to the site of the opening of said hernial sac,
  (f) operating said instrument for grasping and approximating selected portions of said tissue of said hernial sac opening and for joining permanently said approximated portions of said tissue by closing said surgical clip carried by said instrument about said approximated portions,
  (g) monitoring said insertion, maneuvering and operation of said instrument by using said endoscope, and
  (h) removing said instrument from said abdomen while said closed surgical clip remains joining said approximated portions of tissue of said hernial sac.

12. A method according to claim 11 comprising the further steps, after said instrument is removed from said abdomen, of re-loading said instrument with another clip, and repeating steps (d) through (h).

13. A method according to claim 11 wherein said surgical clip has a pair of legs and a tooth extending from each leg, wherein said step of grasping and approximating selected portions of said tissue, comprises operating said instrument to open said surgical clip carried thereon, causing said teeth of said open clip to engage said selected tissue portions, and operating said instrument to close said surgical clip whose teeth pierce said tissue portions, urge said portions together and permanently join said approximated portions.

14. A method for a hernial repair operation for closing the neck opening of a hernial sac having separated tissue portions in the groin area of a patient, said neck opening defined by spaced apart tissue portions thereof, said method including use of a stapling instrument having a body part that is slim with a maximum outside diameter of 6.5 mm and with a length of at least ten inches, said instrument having a pair of jaws at one end and drive means at said opposite end for operating said jaws reversibly between open and closed positions, said instrument being loaded with at least one surgical clip releasable from the instrument, comprising the steps:

(a) creating a puncture wound of approximately one half inch breadth in the abdomen at a site remote from said hernial sac in the groin area, (b) inserting a canula through said puncture wound, (c) inserting said instrument with the jaws end first through said canula, (d) maneuvering said jaws end of the instrument to the site of the opening of said hernial sac, (e) operating said instrument for grasping and approximating selected portions of said tissue of said hernial sac opening and for joining permanently said approximated portions of said tissue by closing said surgical clip carried by said instrument about said approximated portions, (f) monitoring said insertion maneuvering and operation of said instrument by using an endoscope, and (g) removing said instrument from said abdomen while said closed surgical clip remains joining said approximated portions of tissue of said hernial sac.

* * * * *